United States Patent [19]

Cocks

[11] Patent Number: 4,953,732

[45] Date of Patent: Sep. 4, 1990

[54] WASTE MATERIAL COLLECTING BIN

[75] Inventor: David C. Cocks, London, England

[73] Assignee: The Wellcome Foundation Limited, London, England

[21] Appl. No.: 492,349

[22] Filed: Mar. 8, 1990

Related U.S. Application Data

[63] Continuation of Ser. No. 296,242, Jan. 12, 1989, abandoned.

[30] Foreign Application Priority Data

Jan. 13, 1988 [GB] United Kingdom ................. 8800660

[51] Int. Cl.⁵ ............................................. B65D 90/00
[52] U.S. Cl. ................................... 220/502; 220/87.2; 220/262; 220/908
[58] Field of Search .................. 220/1 T, 87, 20.5, 22, 220/23, 262; 141/69, 70

[56] References Cited

U.S. PATENT DOCUMENTS

| | | | |
|---|---|---|---|
| 508,325 | 11/1893 | Lewis | 220/87 |
| 1,092,752 | 4/1914 | Segall | 220/87 |
| 1,323,918 | 12/1919 | Seraphine | 220/87 |
| 1,481,685 | 1/1924 | Burrows | 220/87 X |
| 1,622,853 | 3/1927 | Turnbull | 220/87 |
| 1,695,133 | 12/1928 | Allen | 220/1 T |
| 2,281,630 | 5/1942 | Southard | 220/87 |
| 2,434,238 | 1/1948 | Wolfson | 220/87 |
| 2,540,447 | 2/1951 | Henrikson | 220/87 |
| 2,571,428 | 10/1951 | Drinkhaus | 220/87 |
| 2,652,173 | 9/1953 | Farrell | 220/87 |
| 3,307,902 | 3/1967 | Nardi | 220/87 X |
| 3,322,477 | 5/1967 | Armijo | 312/223 |
| 4,736,860 | 4/1988 | Bemis | 220/1 T |
| 4,828,107 | 5/1989 | Spencer | 220/1 T X |

Primary Examiner—Steven M. Pollard
Attorney, Agent, or Firm—Nixon & Vanderhye

[57] ABSTRACT

A waste material collecting bin has a storage container (24) for containing waste material fed into it via a rotary inlet valve (22). Prior to dropping into the container waste material rests on the valve adjacent the inlet and is there sprayed with treating substance drawn from a reservoir (19).

8 Claims, 3 Drawing Sheets

Fig. 4.
Fig. 5.
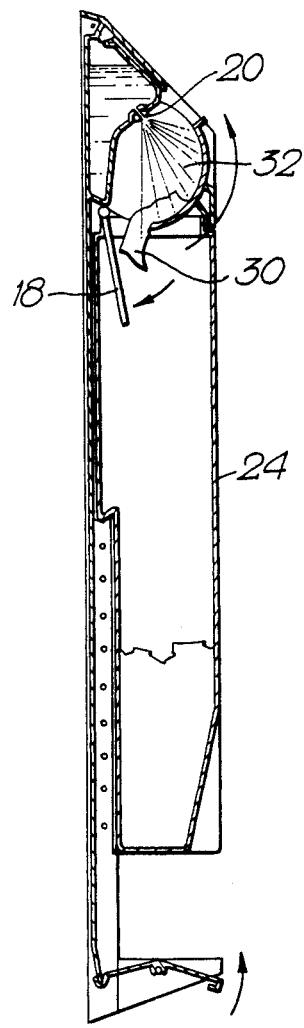
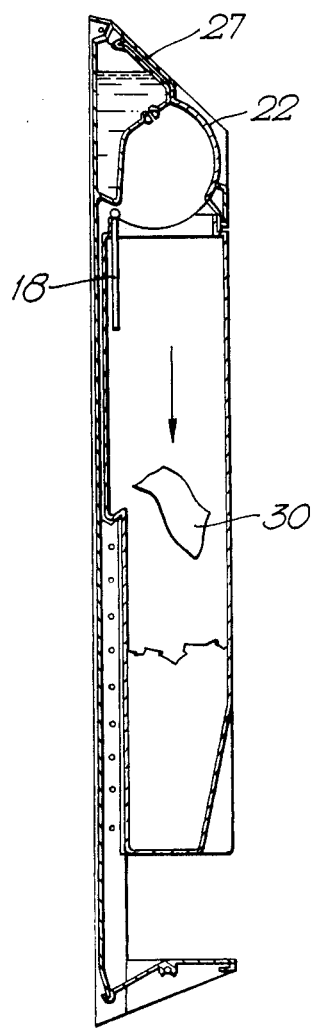

WASTE MATERIAL COLLECTING BIN

This is a continuation of application Ser. No. 07/296,242, filed Jan. 12, 1989, now abandoned.

TECHNICAL FIELD

This invention relates to a collecting bin for the collection and storage of waste material, in particular waste material that is contaminated with blood or other body fluid.

BACKGROUND ART

The collection and short-term storage of catamenial tampons, sanitary towels, soiled nappies and the like body fluid-contaminated waste material poses problems in public toilet facilities, since such waste material is health hazardous and a potential source of odour if not stored under antiseptic conditions.

Proposals have been made for depositing the waste material in a bag-lined bin containing a volume of odour-combatting liquid but this arrangement suffers from the disadvantage that the entire supply of liquid can be absorbed by the early deposited material leaving no liquid available for the later deposited material. To avoid this possibility it has been proposed, in for example GB-A-1598482, GB-A-1515266, GB-A-1105706 and GB-A-1180478, to spray liquid onto the waste material and in certain embodiments, to mount the spray means in or on a lid of the collecting bin so that spraying of liquid can become a coordinated action with removing the lid to deposit waste material in the bin. One embodiment described in GB-A-1180478 has a bottle of liquid mounted above a waste material inlet to the bin with a length of flexible tubing partially obstructing the inlet so that displacement of the tubing by inserted waste material will cause a few drops to be dispensed into the bin.

SUMMARY OF THE INVENTION

This invention is concerned with an improved waste material collecting bin in which means is provided to automatically moisten each article of waste material as it is supported adjacent to the inlet and prior to its falling into the collecting bin.

According to one aspect of the invention a waste material collecting bin comprises a storage container, an inlet to the storage container, a reservoir of a fluent material-treating substance, and means to add fluent substance from the reservoir to waste material added to the container, wherein the inlet includes a support member which temporarily supports the waste material while it is contacted by the fluent substance from the reservoir.

Conveniently, the support member is part of a valve turnably mounted in an upper part of the bin. Suitably the valve is pedal operated. Desirably, as the valve turns into its open position, it exposes an opening through which the waste material can pass and at the same time a platform on which the material can temporarily lodge, and as the valve turns back into its closed position, spray means is actuated to add substance from the reservoir to the waste material before the platform is completely removed from below the waste material allowing the latter to drop suitably treated by the substance (e.g. moistened) into the storage container.

Suitably the closed position of the valve is a position of minimum-stored energy, the opening of the valve being accompanied by a stressing of a spring or a working against the urging of gravity.

Conveniently, the means to add fluent material-treating substance to the waste material includes a spray nozzle communicating with a pump containing the fluent substance drawn from the reservoir. Expulsion of the fluent substance from the pump can be effected by spring means which act to return the valve to the closed position.

In a preferred arrangement a rotary valve is used which is linked to a foot pedal and a liquid pump whereby depressing the foot pedal opens a valve adjacent to the inlet, fills the pump with treating liquid and primes a spring. Release of the foot pedal then allows the spring to empty the pump of liquid (via spray nozzles adjacent to the inlet) as the valve returns to its closed position.

BRIEF DESCRIPTION OF THE DRAWINGS

One embodiment of collecting bin in accordance with the invention will now be described, by way of example, with reference to the accompanying drawings, in which:

FIGS. 2 to 5 show the manner of operation of the bin shown in FIG. 1.

DESCRIPTION OF PREFERRED EMBODIMENT

Figure 1:
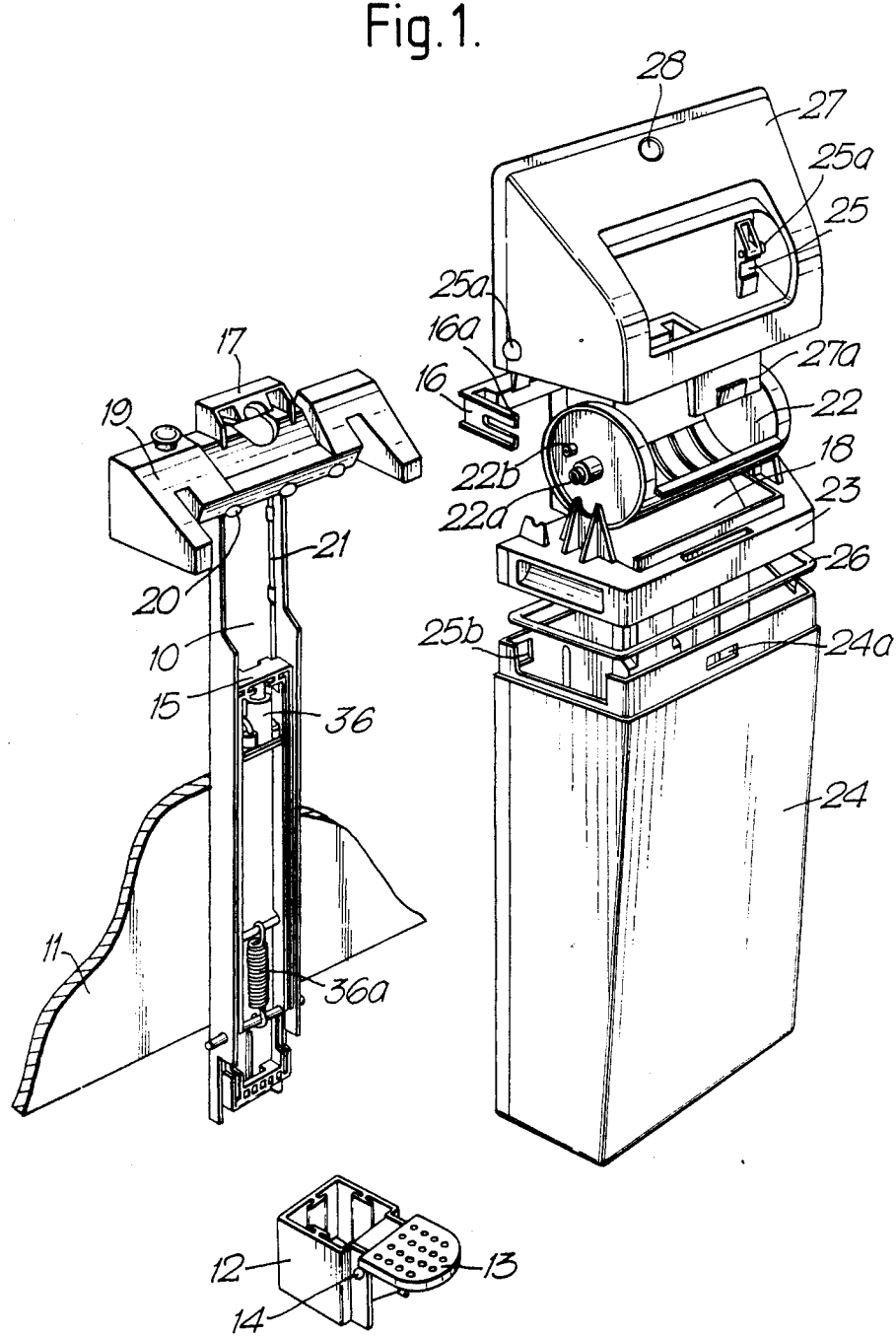
FIG. 1 shows component parts of the bin.

The collection bin shown in FIG. 1 is a device typically having a capacity of 20 or more liters which is adapted to be mounted on a wall or partition. Typical dimensions for A and B in FIG. 2 would be 895 mm and 170 mm, the width of the unit being some 350 mm.

The bin comprises a U-shaped back plate 10 screwed to the wall or partition 11 and supporting a pedal assembly 12. The assembly 12 includes a foot pedal 13 pivotally mounted on a rod 14 and a vertically-extending operating plate 15 which is adapted to push against a cross bar bracket 16 which provides a pair of ears 16a (only one pair of which can be seen in FIG. 1). As the pedal 13 is depressed the plate 15 and bracket 16 are lifted.

A reservoir bottle 19 containing waste material-treating liquid is located on the back plate 10 at the top end thereof and a piston-in-cylinder pump 36 is located part-way down the base plate 10. The bottle 19 is linked by a pipe 21 to the inlet of the cylinder in the pump 36 and the outlet from the cylinder of the pump 36 is linked to an array of spray openings 20 via a second pipe (not shown). When the plate 15 is lifted, against the urging of a spring 36a, the piston in the cylinder of the pump 36 makes a stroke which draws liquid from the bottle 19 into the cylinder of the pump 36. Lifting of the plate 15 also turns a part-cylindrical valve plate 22, turnably mounted by stub-axles 22a, in a valve unit 23. The valve unit 23 is removably clipped onto the open upper end of a storage container 24 and by means of a liner frame 26 the perimeter of a disposable plastic bag (not shown) is supported within the container 24. A boss 22b on each side of the valve plate 22 engages in the ears 16a of the bracket 16 so that upward movement of the plate 15 causes turning of the valve plate 22 about its stub axles 22a towards its open position (shown in FIGS. 1 and 3).

A decorative cover 27 hides, inter alia, the plate 15, the reservoir bottle 19 and the circular ends of the valve plate 22 and is clipped onto the upper end of the container 24 by means of a pair of clips 25 pivotally mounted on spindles 25a and a tongue 27a which passes through the valve unit 23 and engages in a recess 24a in the container 24. The clips 25 engage one in each of two openings 25b in the upper part of the container 24.

The complete collection bin unit is locked onto the partition or wall 11 by a centrally mounted lock 28 which engages with a locking plate 17 on the reservoir bottle 19.

To prevent users seeing into the interior of the plastic bag lining the container 24 during a dispensing operation, a pivotally mounted shielding flap 18 can be provided which normally depends freely down into the container 24 but which turns upwardly as the valve plate 22 opens and returns to the downwardly depending position as the valve plate 22 recloses. The movement of the flap 18 can be caused by providing a cam surface on one circular end of the valve plate 22 which moves the flap as the valve plate turns.

Figure 2:
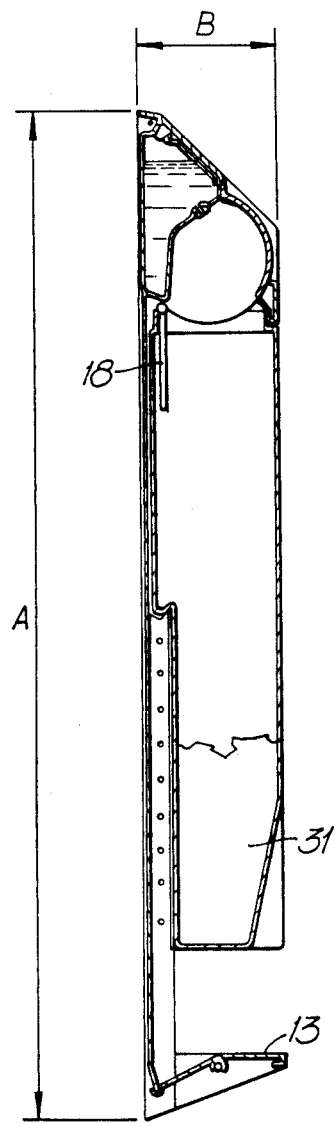

FIGS. 2 and 5 show the valve plate 22 fully closed, the flap 18 vertical and the pedal 13 in its uppermost position.

Figure 3:
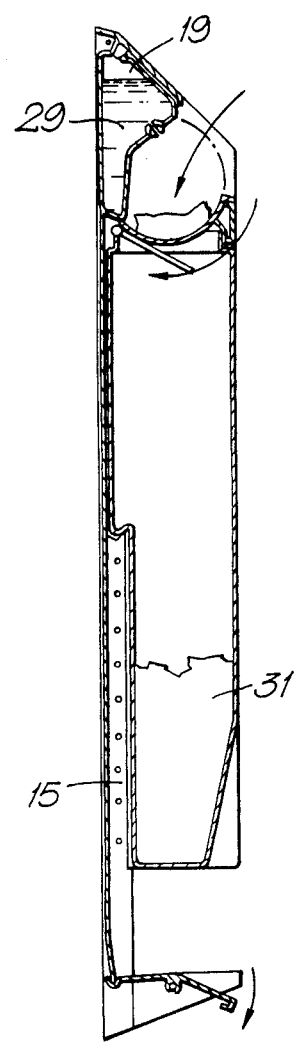

FIG. 3 shows the valve plate 22 fully open and FIG. 4 shows the valve plate 22 closing, in both cases with the flap 18 partly obstructing the entrance to the container 24.

Method of Use

FIGS. 2 to 5 show how the unit is used in a series of sequential cross-sectional views. The liquid in the reservoir bottle 19 (e.g. a disinfectant and/or perfume mixture) is shown at 29 and a sanitary towel at 30. Previously added towels are shown at 31. The spray 32 shown in FIG. 4 is generated by the pedal-induced pressure transmitted via the ears 16a and spring 36a and lasts long enough to moisten the towel 30 while it lies on the valve plate 22 prior to falling into the container 24.

Although primarily intended for the collection or sanitary towels—the units described (or smaller and/or free standing versions) can be used in veterinary, dentists' or general practitioners' surgeries, or in hospital wards. In surgeries or wards, the unit can be used to collect a wide range of different sorts of waste material that because they may be contaminated with blood, need to be disposed of carefully.

I claim:
1. A waste material collecting bin, comprising:
a storage container;
an inlet to said storage container;
a reservoir of a fluent material-treating substance;
fluent addition means for adding said fluent substance from said reservoir to waste material added to said container; and
an arcuate support means provided in said inlet for temporarily supporting waste material while it is contacted by said fluent substance from said reservoir, said fluent addition means being disposed above said arcuate support means such that said fluent substance is added to the waste material temporarily supported on said arcuate support means from above.

2. A collecting bin as claimed in claim 1, in which the support member is part of a valve closing the inlet and turnably mounted in an upper part of the bin.

3. A collecting bin as claimed in claim 2, in which the valve is pedal operated.

4. A collecting bin as claimed in claim 2 in which as the valve turns into its open position, it exposes an opening through which the waste material can pass and at the same time exposes a platform on which the waste material can temporarily lodge, whereby as the valve turns back into its closed position, spray means is actuated to add substance from the reservoir to the waste material before the platform is completely removed from below the waste material allowing the latter to drop suitably treated by the sprayed substance into the storage container.

5. A collecting bin as claimed in claim 2 in which the closed position of the valve is a position of minimum-stored energy, the opening of the valve being accompanied by a stressing of a spring which effects addition of the fluent material as it returns to its unstressed condition during closing of the valve.

6. A collecting bin as claimed in claim 1, in which the means to add fluent material-treating substance to the waste material includes a spray nozzle communicating with a pump containing fluent substance drawn from the reservoir.

7. A collecting bin as claimed in claim 6, in which expulsion of the fluent substance from the pump is effected by spring means which act to return the valve to the closed position.

8. A collecting bin as claimed in claim 1, in which a rotary valve is used to close the inlet, this valve being linked to a foot pedal and a liquid pump whereby depressing the foot pedal opens the rotary valve adjacent to the inlet, fills the pump with treating liquid and primes a spring, release of the foot pedal then allowing the spring to empty the pump of liquid, via spray nozzles adjacent to the inlet, as the valve returns to its closed position.

* * * * *